US012338270B2

United States Patent
Lee et al.

(10) Patent No.: US 12,338,270 B2
(45) Date of Patent: Jun. 24, 2025

(54) PHARMACEUTICAL COMPOSITION COMPRISING POLYPEPTIDE

(71) Applicant: D&D Pharmatech Inc., Gyunggi-do (KR)

(72) Inventors: Kang Choon Lee, Seoul (KR); Og Yi Park, Germantown, MD (US); Hyoung Tae An, Gyeonggi-do (KR); Eun Ji Park, Seoul (KR); Jae Hee Shin, Seoul (KR); Sung Mook Lim, Seoul (KR)

(73) Assignee: D&D Pharmatech Inc., Gyunggi-do (KR)

( * ) Notice: Subject to any disclaimer, the term of this patent is extended or adjusted under 35 U.S.C. 154(b) by 948 days.

(21) Appl. No.: 17/261,144

(22) PCT Filed: Jul. 19, 2019

(86) PCT No.: PCT/KR2019/008918
§ 371 (c)(1),
(2) Date: Jan. 18, 2021

(87) PCT Pub. No.: WO2020/017916
PCT Pub. Date: Jan. 23, 2020

(65) Prior Publication Data
US 2021/0317178 A1   Oct. 14, 2021

(30) Foreign Application Priority Data

Jul. 19, 2018 (KR) .................. 10-2018-0083946
May 23, 2019 (KR) .................. 10-2019-0060513

(51) Int. Cl.
| | |
|---|---|
| *C07K 14/605* | (2006.01) |
| *A61K 47/60* | (2017.01) |
| *A61K 47/69* | (2017.01) |
| *A61P 1/16* | (2006.01) |
| *A61P 3/04* | (2006.01) |
| *A61P 3/10* | (2006.01) |
| *A61K 38/00* | (2006.01) |

(52) U.S. Cl.
CPC ............ *C07K 14/605* (2013.01); *A61K 47/60* (2017.08); *A61K 47/6941* (2017.08); *A61P 1/16* (2018.01); *A61P 3/04* (2018.01); *A61P 3/10* (2018.01); *A61K 38/00* (2013.01)

(58) Field of Classification Search
CPC .. C07K 14/605; A61K 47/60; A61K 47/6941; A61K 38/00; A61P 1/16; A61P 3/04; A61P 3/10
See application file for complete search history.

(56) References Cited

U.S. PATENT DOCUMENTS

| | | | |
|---|---|---|---|
| 7,141,547 B2 | 11/2006 | Rosen | |
| 8,110,665 B2 | 2/2012 | Kim | |
| 8,273,854 B2 | 9/2012 | Glaesner | |
| 2011/0152182 A1 | 6/2011 | Alsina-Fernandez | |
| 2014/0212440 A1* | 7/2014 | Jung | A61K 47/6801 424/178.1 |

FOREIGN PATENT DOCUMENTS

| | | | |
|---|---|---|---|
| CA | 3021933 | 10/2017 | |
| KR | 100925017 | 11/2009 | |
| KR | 101665009 | 9/2016 | |
| KR | 101990075 | 6/2019 | |
| WO | 2012169798 | 12/2012 | |
| WO | 2012173422 | 12/2012 | |
| WO | WO-2012173422 A1 * | 12/2012 | ............ A61K 38/00 |
| WO | 2014017843 | 1/2014 | |
| WO | 2014073842 | 5/2014 | |
| WO | 2014073845 | 5/2014 | |
| WO | 2015183054 | 12/2015 | |
| WO | 2017003191 | 1/2017 | |

OTHER PUBLICATIONS

Cheang, et al., "Glucagon-like Peptide-1 (GIP-1 )-Based Therapeutics: Current Status and Future Opportunities beyond Type 2 Diabetes", Chemmedchem Communications, 13(7):662-671 (2018).
Day, J. w. et al., "A new glucagon and GLP-1 co-agonist eliminates obesity in rodents", Nature Chemical Biology, 5(10): 749-757 (2009).
International Search Report for PCT/KR2019/008918 dated Oct. 29, 2019.
Day, et al., "A new glucagon and GLP-1 co-agonist eliminates obesity in rodents", *Nature Chemical Biology*, 5(10): 749-757 (2009).

\* cited by examiner

*Primary Examiner* — Sudhakar Katakam
(74) *Attorney, Agent, or Firm* — PABST PATENT GROUP LLP

(57) ABSTRACT

The present invention relates to a pharmaceutical composition including a polypeptide, and more particularly, to a pharmaceutical composition for preventing or treating obesity, diabetes, or non-alcoholic fatty liver disease. The pharmaceutical composition is safe without any side effects such as vomiting or nausea, and has effects of reducing food intake, enhancing insulin secretion, suppressing gastric emptying, promoting lipolysis, and lowering a level of triglycerides.

17 Claims, 5 Drawing Sheets

Specification includes a Sequence Listing.

[Fig. 1]
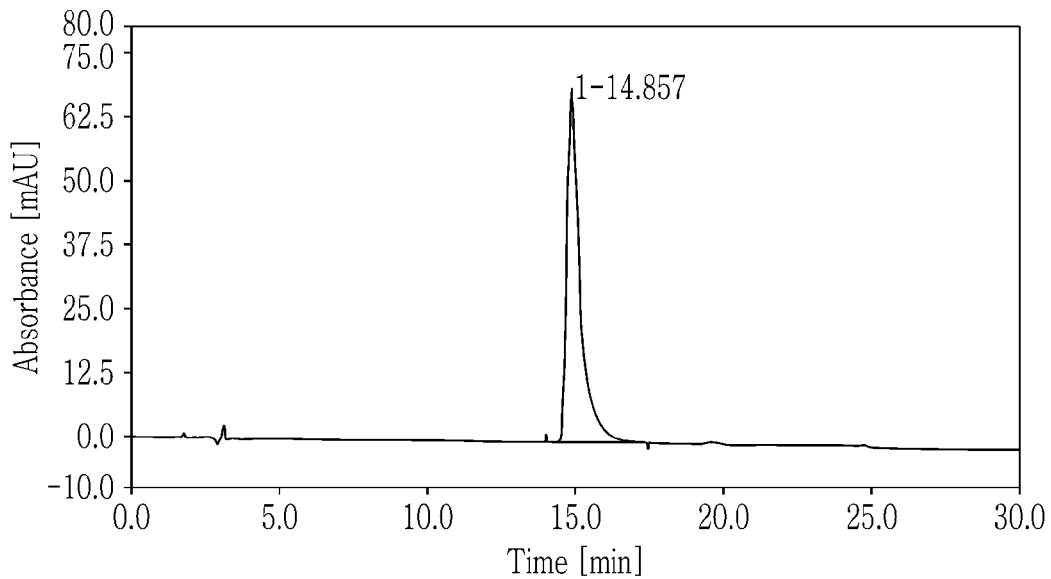
[Fig. 2]
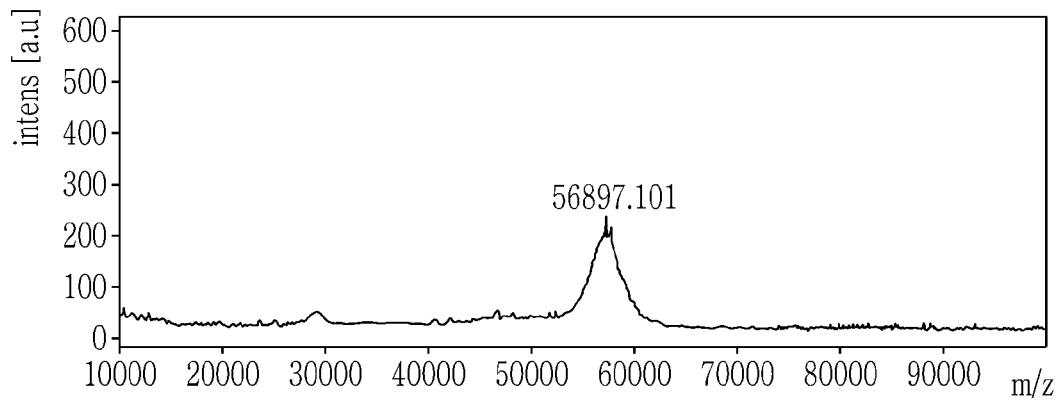
[Fig. 3]
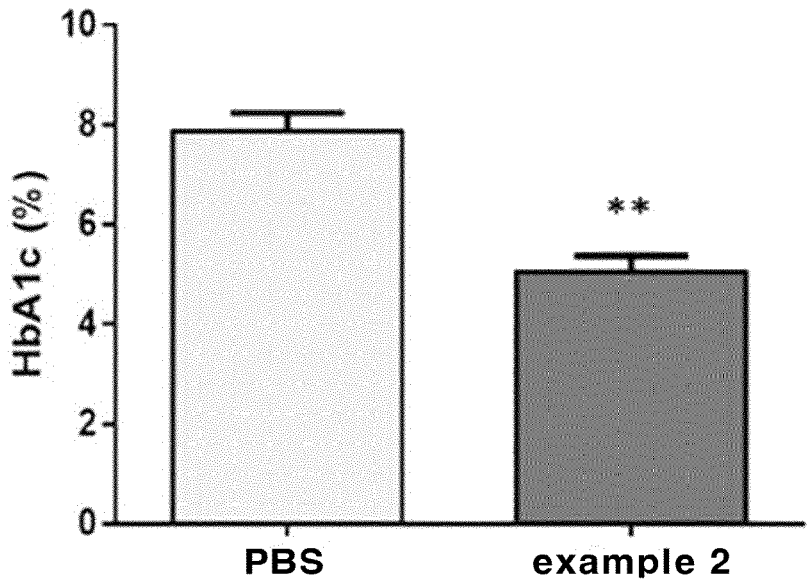

[Fig. 4]
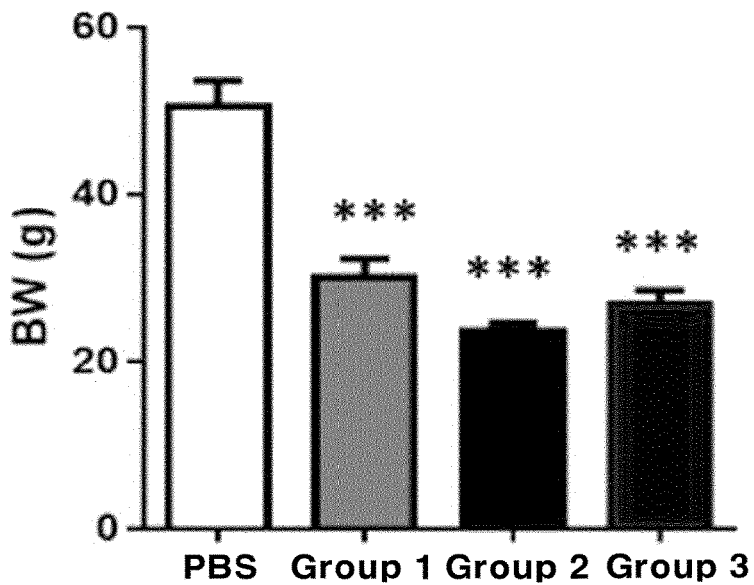
[Fig. 5]
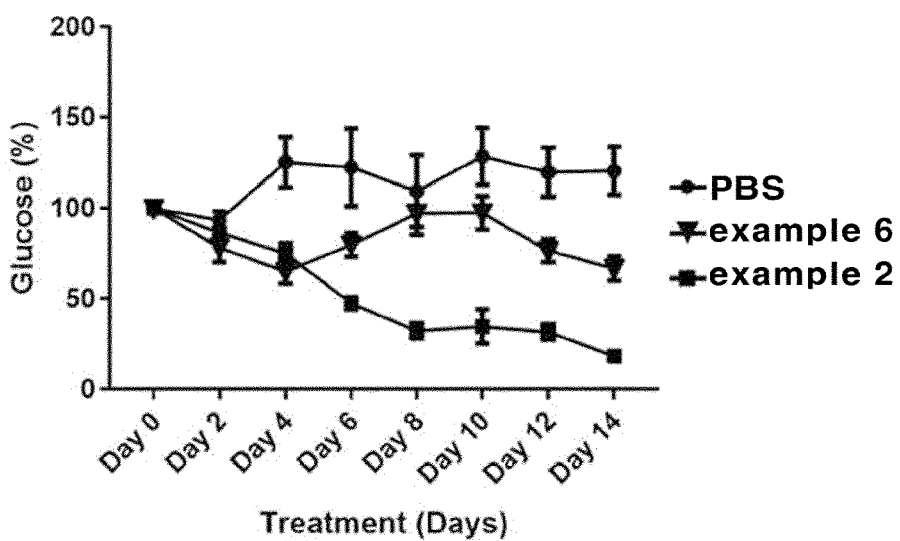
[Fig. 6]
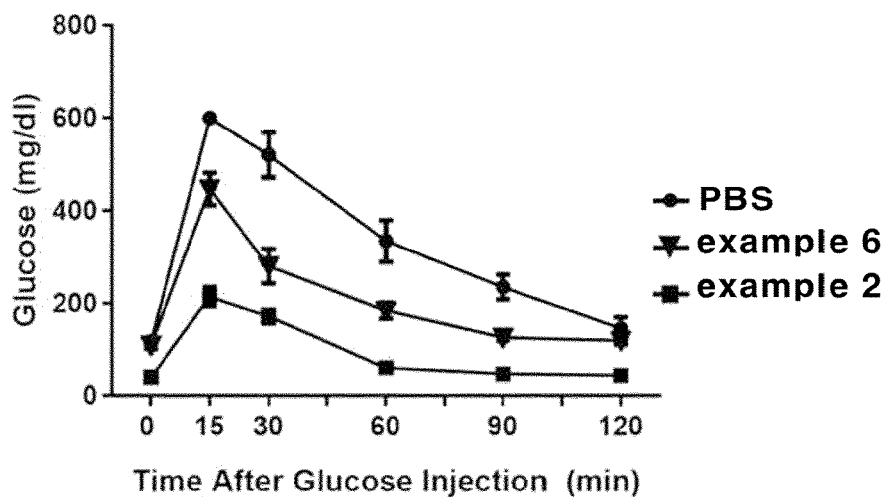

[Fig. 7]
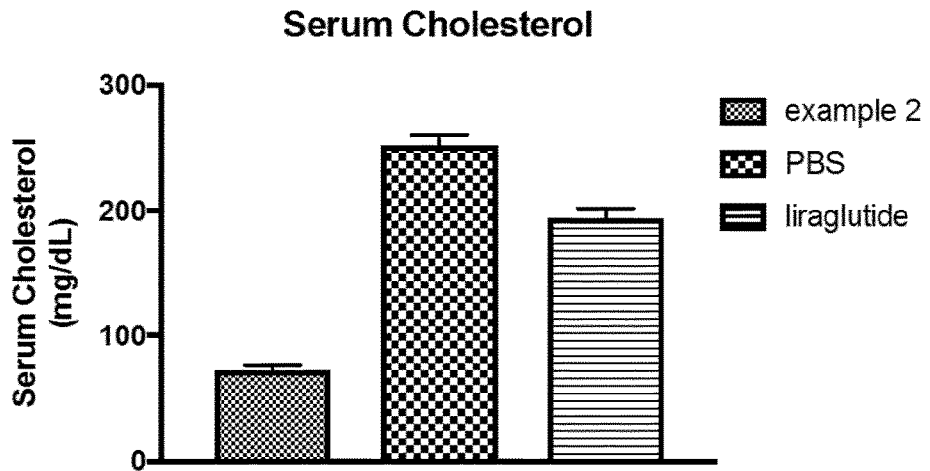
[Fig. 8]
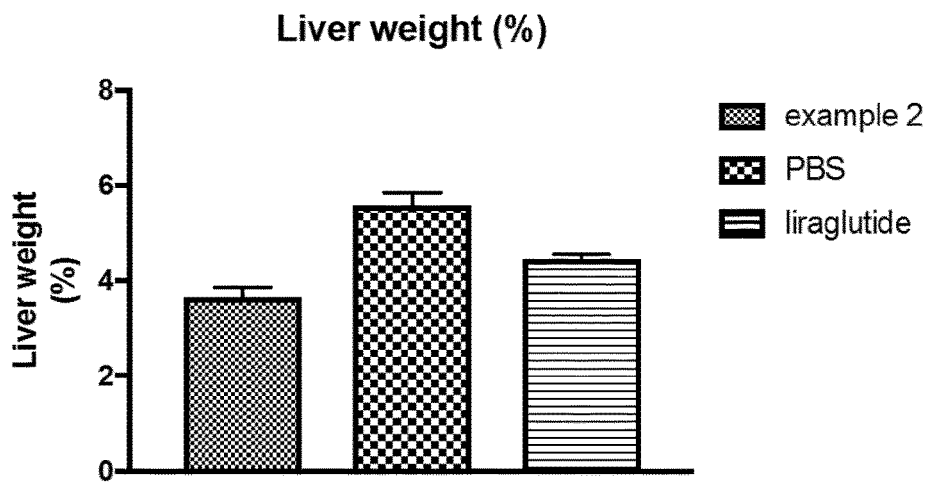
[Fig. 9]
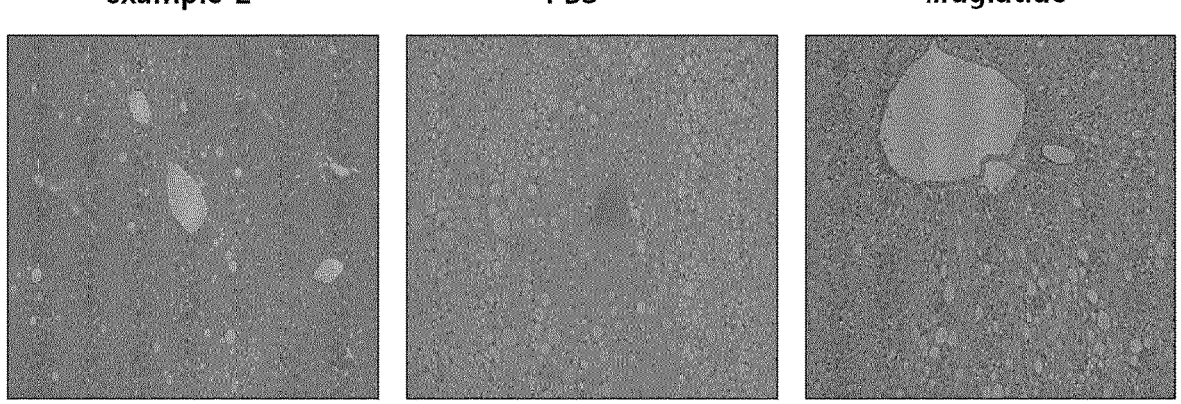

[Fig. 10]
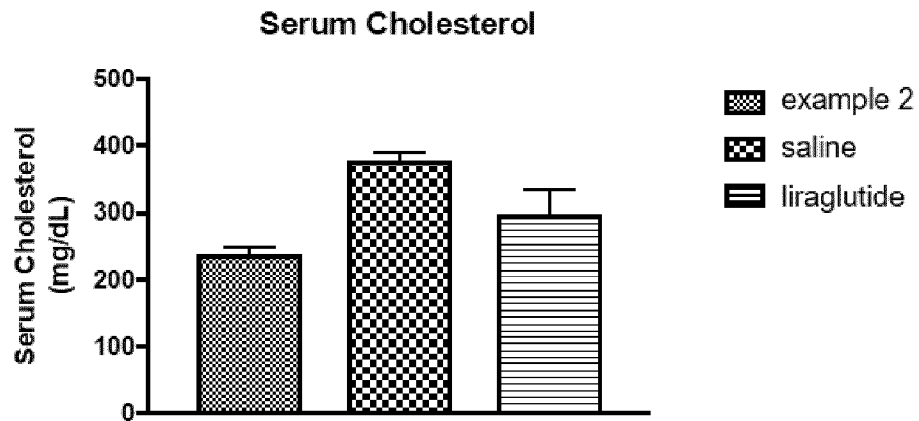
[Fig. 11]
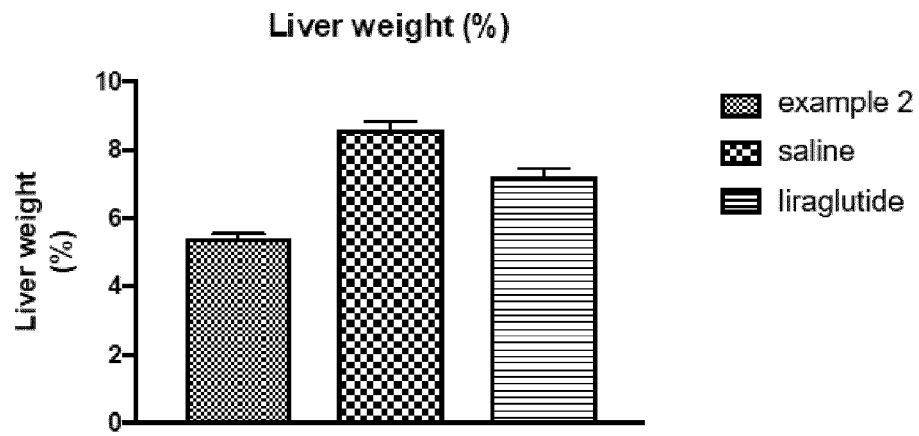
[Fig. 12]
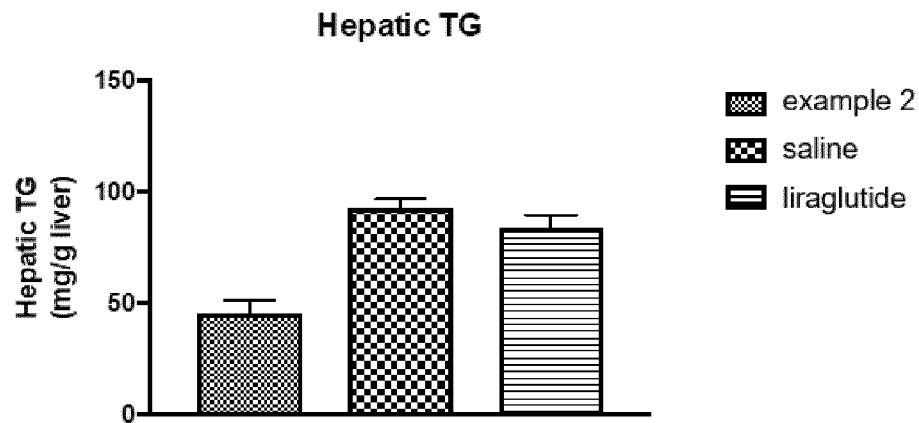

[Fig. 13]
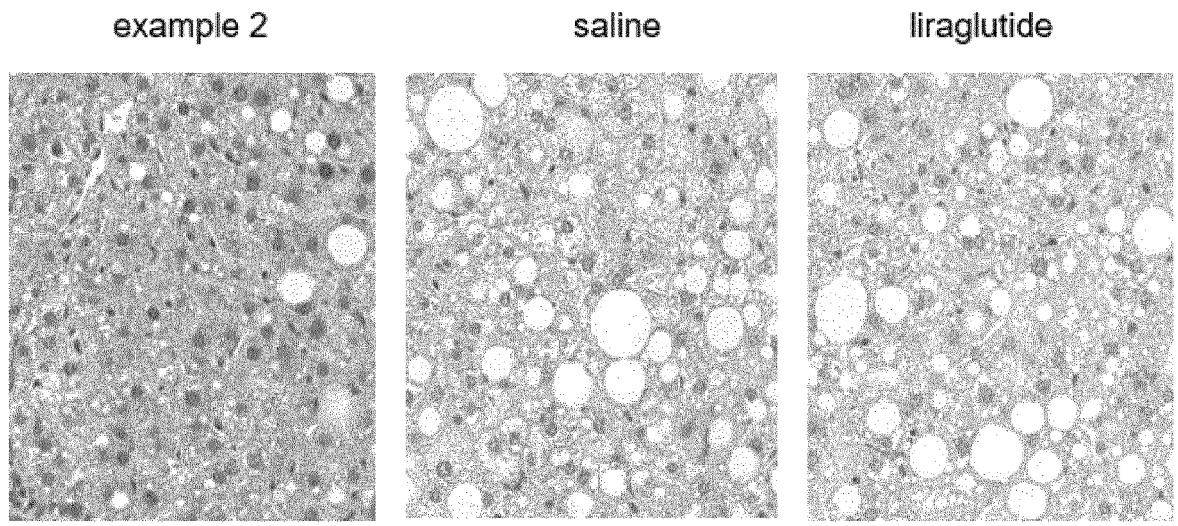
[Fig. 14]
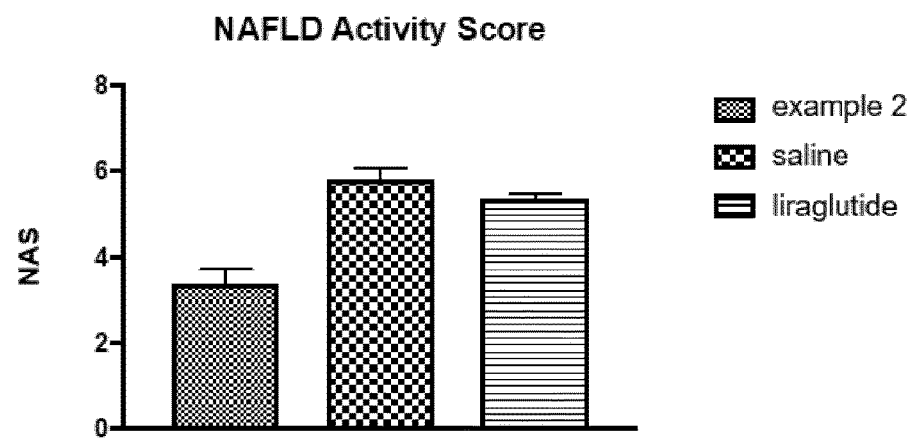

SEQUENCE LISTING

```
<160> NUMBER OF SEQ ID NOS: 12

<210> SEQ ID NO 1
<211> LENGTH: 29
<212> TYPE: PRT
<213> ORGANISM: Unknown
<220> FEATURE:
<223> OTHER INFORMATION: Glucagon

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 30
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: Xaa = aminoisobutyric acid (Aib)
<222> LOCATION: (2)..(2)

<400> SEQUENCE: 2

His Xaa Gln Gly Thr Phe Thr Ser Asp Tyr Ser Lys Tyr Leu Asp Glu
1               5                   10                  15

Gln Ala Ala Lys Glu Phe Val Gln Trp Leu Met Asn Thr Cys
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic peptide

<400> SEQUENCE: 3

His Gly Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa = aminoisobutyric acid (Aib)
<222> LOCATION: (2)..(2)

<400> SEQUENCE: 4

His Xaa Gln Gly Thr Phe Thr Ser Asp Tyr Ser Lys Tyr Leu Asp Glu
1               5                   10                  15

Glu Ala Val Lys Glu Phe Val Gln Trp Leu Met Asn Thr Cys
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

His Gly Gln Gly Thr Phe Thr Ser Asp Tyr Ser Lys Tyr Leu Asp Glu
1               5                   10                  15

Glu Ala Val Lys Glu Phe Val Gln Trp Leu Met Asn Thr Cys
            20                  25                  30

<210> SEQ ID NO 6
<211> LENGTH: 30
<212> TYPE: PRT
<213> ORGANISM: Unknown
<220> FEATURE:
<223> OTHER INFORMATION: GLP-1

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
```

<210> SEQ ID NO 7
<211> LENGTH: 27
<212> TYPE: PRT
<213> ORGANISM: Artificial Sequence
<220> FEATURE:
<223> OTHER INFORMATION: Synthetic peptide

<400> SEQUENCE: 7

Gln Gly Thr Phe Thr Ser Asp Tyr Ser Lys Tyr Leu Asp Glu Lys Arg
1               5                   10                  15

Ala Lys Glu Phe Val Gln Trp Leu Met Asn Thr
            20                  25

<210> SEQ ID NO 8
<211> LENGTH: 27
<212> TYPE: PRT
<213> ORGANISM: Artificial Sequence
<220> FEATURE:
<223> OTHER INFORMATION: Synthetic peptide

<400> SEQUENCE: 8

Gln Gly Thr Phe Thr Ser Asp Tyr Ser Lys Tyr Leu Asp Glu Gln Ala
1               5                   10                  15

Ala Lys Glu Phe Val Gln Trp Leu Met Asn Thr
            20                  25

<210> SEQ ID NO 9
<211> LENGTH: 27
<212> TYPE: PRT
<213> ORGANISM: Artificial Sequence
<220> FEATURE:
<223> OTHER INFORMATION: Synthetic peptide

<400> SEQUENCE: 9

Gln Gly Thr Phe Thr Ser Asp Tyr Ser Lys Tyr Leu Asp Glu Glu Ala
1               5                   10                  15

Val Lys Glu Phe Val Gln Trp Leu Met Asn Thr
            20                  25

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Glu Lys Arg Ala Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Glu Gln Ala Ala Lys
1               5

<210> SEQ ID NO 12
<211> LENGTH: 5

```
<212> TYPE: PRT
<213> ORGANISM: Artificial Sequence
<220> FEATURE:
<223> OTHER INFORMATION: Synthetic peptide

<400> SEQUENCE: 12

Glu Glu Ala Val Lys
1               5
```

PHARMACEUTICAL COMPOSITION COMPRISING POLYPEPTIDE

CROSS-REFERENCE TO RELATED APPLICATIONS

This application is a National Phase application under 35 U.S.C. 371 of PCT/KR2019/008918, filed Jul. 19, 2019, and claims the benefit of and priority to Korean Applications 10-2018-0083946 filed Jul. 19, 2018 and 10-2019-0060513 filed May 23, 2019, the disclosures of which are hereby incorporated herein by reference in their entirety.

REFERENCE TO SEQUENCE LISTING

The Sequence Listing submitted Jan. 18, 2021, as a text file named "DDP_100_PCT_ST25.txt," created on Jan. 15, 2021, and having a size of 4,266 bytes is hereby incorporated by reference.

TECHNICAL FIELD

The present invention relates to a pharmaceutical composition including a polypeptide and their medical use, for example in the treatment or prevention of obesity, diabetes, or non-alcoholic fatty liver disease. The polypeptide has effects of reducing food intake, enhancing insulin secretion, suppressing gastric emptying, promoting lipolysis, and lowering a level of triglycerides without side effects such as vomiting or nausea.

BACKGROUND ART

Recently, with economic development and the high growth of scientific technology, aging populations are growing and adult diseases are rapidly increasing. This is caused by stress, poor eating habits, excessive calorie intake, and reduced physical activity. Mortality rates of heart and cerebrovascular diseases, which are complications accompanying obesity, are ranked as first and second, and obesity is suggested as a cause of various adult diseases such as diabetes, non-alcoholic fatty liver disease, and the like.

Obesity refers to a state in which fat is accumulated at higher amounts than normal, and the most accurate method for evaluation of obesity is to measure body fat mass. However, accurate measurement of fat mass is costly, and thus it is evaluated using indirect methods. The most commonly used indirect methods are to measure body mass index (BMI) and waist circumference. The World Health Organization (WHO) announced classifications based on data relating BMI to mortality risk, which are based on normal weight: 18.5 to 24.9 $kg/m^2$, overweight: 25 to 29.9 $kg/m^2$, and obesity: 30 $kg/m^2$ or more.

The causes of obesity are known as energy imbalances due to excessive calorie intake and relatively decreased activities, and the resulting increase in body fat. However, it is difficult to assign only one factor because various risk factors such as eating habit, lifestyle, age, race, genetic factors, and the like are involved in obesity.

Diabetes are classified into insulin-dependent diabetes (type I diabetes), insulin-independent diabetes (type II diabetes), and malnutrition-related diabetes mellitus (MRDM). The type II diabetes which accounts for more than 90% of diabetic patients are metabolic diseases characterized by the hyperglycemia, and are reported to be caused by decreased insulin secretion of pancreatic beta cells or increased insulin resistance in peripheral tissues due to genetic, metabolic, and environmental factors. In this regard, when body fat increases, the insulin sensitivity is decreased, especially accumulation of abdominal fat is known to be related to glucose intolerance. Also, it is known that insulin resistance is closely correlated with obesity in patients suffering from type II diabetes, with the more severe the obesity, the greater the insulin resistance.

Non-alcoholic fatty liver diseases (NAFLD) refer to a series of diseases including simple steatosis with excessive accumulation of fat in the liver cells independent of alcohol consumption, non-alcoholic steatohepatitis (NASH) including hepatocellular injury (hepatocellular ballooning), inflammation, fibrosis, and, in more advanced cases, cirrhosis. The prevalence rate of non-alcoholic fatty liver disease is rapidly increasing with the increase in the prevalence rate of obesity all over the world, and although the prevalence rate of diabetes varies from country to country, it accounts for about 20 to 30% of the total populations in Western countries, and the incidence rate thereof reaches about 16% in Korea.

Non-alcoholic fatty liver disease shows a close association with the metabolic syndromes including obesity, type II diabetes, dyslipidemia, and the like based on insulin resistance. In fact, it is known that many pre-diabetic and type II diabetic patients have shown to present with non-alcoholic fatty liver/non-alcoholic steatohepatitis, and the rate of progression to liver cirrhosis and liver cancer (i.e., hepatocellular carcinoma) is high in these patients. Meanwhile, the prevalence of diabetes in non-alcoholic fatty liver disease patients is high, and it is evident in non-alcoholic steatohepatitis patients.

Obese patients are primarily advised to control their weight through healthier diet and physical activity, but when these methods are not effective, patients can be treated with medication or surgery.

The current market for anti-obesity drugs is estimated to reach more than approximately one billion dollars, and is growing by about 10% every year. Medicines mainly used as anti-obesity drugs are anorectic agents (lorcaserine, phentermine, etc.) that are classified as psychotropic drugs, most of which act on the central nervous system. Such medicines are known to exhibit an effect of suppressing patients' appetite to lose body weight, but have side effects such as abuse and addictiveness, palpitations, anxiety, insomnolence, and the like when used for a long period of time.

Xenical is one of the medicines that is used as an anti-obesity drug that is not a psychotropic drug. Pancreatic lipase acts as a key enzyme that breaks down a triglyceride into 2-monoacylglycerol and fatty acid. A representative pancreatic lipase inhibitor is tetrahydrolipstatin (orlistat) that is a derivative of lipstatin derived from *Streptomyces toxitricini*, and has a high level of efficacy in inhibiting the absorption of approximately 30% of ingested fats. At present, the tetrahydrolipstatin (orlistat) is commercially available as medication, but has side effects such as gastrointestinal disturbance, anaphylaxis, cholestasis, and the like. Therefore, there are few therapeutic agents that can be safely used with obese patients.

In drug therapy for treating non-alcoholic fatty liver diseases, medications act on mechanisms of aggravating the non-alcoholic fatty liver disease, such as insulin resistance, oxidative stress, apoptosis, inflammatory cytokines, and the like, and inhibit progression of non-alcoholic fatty liver diseases. Among these, it is known that antidiabetic agents have an effect of improving fatty liver as well as the blood glucose lowering effect by improving the common physiopathology states against the onset of fatty liver. However, because no drugs are approved as indications for treating fatty liver disease so far, there is an unmet medical need for development of efficacious therapeutic agents.

Meanwhile, attention is currently focused on the glucagon derivatives. Glucagon is produced in the pancreas when a level of blood glucose starts to drop due to drug treatment, diseases, hormone or enzyme deficiency, etc. Glucagon stimulates the liver to release glucose by breaking down glycogen, and serves to elevate a level of blood glucose to a normal level. In addition to the blood glucose-elevating effect, glucagon is also reported to suppress appetite and activate a hormone-sensitive lipase in fat cells to promote the degradation of fats, thereby exhibiting an anti-obesity effect. As one of such glucagon derivatives, glucagon-like peptide-1 (GLP-1) is a substance that is still under development as a therapeutic agent for alleviating hyperglycemia in diabetic patients, and functions to promote insulin synthesis and secretion, inhibit secretion of glucagon, suppress gastric emptying, facilitate use of glucose, and inhibit food intake. Also, it is known that exendin-4 made from lizard venom, which has approximately 50% amino acid homology to GLP-1, serves to activate a GLP-1 receptor to alleviate hyperglycemia in the diabetic patients. However, it is reported that the GLP-1 receptor agonists for treating obesity or diabetes have a problem in that they cause side effects such as vomiting and nausea.

As an alternative to the GLP-1, oxyntomodulin that can bind to both GLP-1 and glucagon receptors have come into the spotlight. The oxyntomodulin is a peptide that is derived from a precursor of glucagon (i.e., pre-glucagon), shows effects of suppressing food intake by GLP-1, inhibiting glyconeogenesis in liver to regulate a level of blood glucose, and improving satiety, and has a lipolytic function of glucagon. Therefore, the oxyntomodulin has a high probability as an anti-diabetic and anti-obesity drug.

Based on the dual functions of the oxyntomodulin peptide, research for development of drugs for treating diabetes and obesity is being actively conducted. For example, Registered Korean Patent No. 925017 discloses a pharmaceutical composition for oral, parenteral, mucosal, rectal, subcutaneous, or percutaneous administration to treat the excess weight in human beings, which includes oxyntomodulin as an active ingredient. However, it is reported that an anti-obesity drug including the oxyntomodulin has a short in vivo half-life, and exhibits a low level of therapeutic effect on obesity even when administered three times a day at a high dose.

Meanwhile, there are ongoing attempts to overcome the short in vivo half-life of the therapeutic peptide to preserve a high level of pharmacological effect for a long period of time and to maximize the effect of therapeutic agent accordingly. U.S. Pat. No. 7,141,547 discloses fusion proteins of GLP-1 and its analogues with albumin using a recombinant DNA technique, and U.S. Pat. No. 8,273,854 discloses fusion proteins of GLP-1 and its analogues with an immunoglobulin fragment (Fc). These techniques partially improved the short in vivo half-life of the peptide, but are not free from immunogenicity-related problems caused through the administration of proteins that are not native to the human body. As a result, the techniques have a drawback in that the pharmacological effect of the drugs may be lowered when the drugs are administered for a long period of time. Also, there are additional issues in that they require large-scaled cell culture and purification systems for production of the drugs, and it may be difficult to control the quality of the drugs because the drugs may have impurities derived from host cells in terms of the nature of recombinant proteins and may not be exactly the same for each batch. Also, when a peptide having a disulfide bond, such as calcitonin, is used, there is a drawback in that the yield may be lowered due to misfolding. Further, it is difficult to produce a drug by recombinant protein production method when it has unnatural amino acid residues.

Meanwhile, U.S. Pat. No. 8,110,665 discloses a peptide whose short half-life is improved by preparing a conjugate using a non-peptidic polymer and an immunoglobulin fragment (Fc). However, this patent describes a complex production process, which includes producing a biologically active peptide, a non-peptidic polymer, and an immunoglobulin fragment separately, and combining the peptide, polymer, and the immunoglobulin fragment together, which introduces issues such as residual by-products, and decreased yield.

Meanwhile, the PEGylation of therapeutic peptides and proteins is the most potent pharmaceutical technique to improve in vivo half-life. The PEGylation of the peptides and proteins serves to increase their molecular weights, protect a proteolytic site, and mask an immunogenic site, which results in increased in vivo half-lives of the drugs, and reduced immunogenicity of the peptides and proteins. Therefore, the PEGylation technique is effective in enhancing a therapeutic effect by solving the problems regarding the peptide drugs. Owing to these advantages, the PEGylation of the peptides and proteins plays an important role in enhancing the therapeutic effect in the drug delivery system.

However, a method using PEG has drawbacks in that PEGylation reduces activity of peptide drugs and produces a low yield due to poor reactivity to peptides with an increasing molecular weight of PEG. In this regard, there is a need for a method of PEGylation by means of a simple production process and a high selectivity reaction.

Therefore, there are demands for a therapeutic agent for treating obesity, diabetes, or non-alcoholic fatty liver disease, which has effects of reducing food intake, enhancing insulin secretion, suppressing gastric emptying, promoting lipolysis, and lowering a level of triglycerides without any side effects such as vomiting or nausea, and is able to be obtained in high yield by optimizing a preparation method.

PRIOR-ART DOCUMENTS

Patent Documents

Patent Document 1: Registered Korean Patent No. 0925017 entitled "Oxyntomodulin for Preventing or Treating Excess Weight"

Patent Document 2: Registered U.S. Pat. No. 7,141,547 entitled "Albumin Fusion Proteins Comprising GLP-1 Polypeptides"

Patent Document 3: Registered U.S. Pat. No. 8,273,854 entitled "GLP-1 Analog Fusion Proteins"

Patent Document 4: Registered U.S. Pat. No. 8,110,665 entitled "Pharmaceutical Composition Comprising an Immunoglobulin FC Region as a Carrier"

Patent Document 5: Registered Korean Patent No. 1665009 entitled "Pharmaceutical Composition for Preventing or Treating Non-alcoholic Fatty Liver Diseases"

DISCLOSURE OF INVENTION

Technical Problem

To solve the above problems, the present inventors have conducted research and efforts to develop a therapeutic agent for treating obesity, diabetes, or non-alcoholic fatty liver disease, which is safe and also has effects of reducing food intake, enhancing insulin secretion, suppressing gastric emptying, promoting lipolysis, and lowering a level of triglycerides without any side effects such as vomiting or nausea, and also to develop a method capable of preparing the therapeutic agent in high yield, and prepare a polypeptide having an amino acid sequence represented by the following General Formula 1. As a result, the present inventors have confirmed that a composition including the polypeptide has an excellent effect of preventing or treating obesity, diabetes, or non-alcoholic fatty liver disease, and a site-specific conjugate with the polypeptide and non-peptidic polymer has a superior effect of preventing or treating obesity, diabetes, or non-alcoholic fatty liver disease via increasing the half-life of the polypeptide in blood while maintaining the in vivo activity of the polypeptide, thereby completing the present invention.

[General Formula 1]
(SEQ ID NOs. 7-9)
R1-X1-QGTFTSDYSKYLD-R2-EFVQWLMNT-R3, wherein R1 is histidine, desamino-histidyl, N-dimethylhistidyl, beta-hydroxyimidazopropionyl, 4-imidazoacetyl, or beta-carboxy imidazopropionyl;

X1 is a deletion, glycine, or aminoisobutyric acid (Aib);

R2 is EKRAK (SEQ ID NO. 10), EQAAK (SEQ ID NO. 11), or EEAVK (SEQ ID NO. 12); and R3 is a deletion, cysteine, lysine, or methionine.

Therefore, it is an object of the present invention to provide a pharmaceutical composition including a polypeptide for preventing or treating obesity, diabetes, or nonalcoholic fatty liver disease.

Solution to Problem

To solve the above problems, a pharmaceutical composition according to one exemplary embodiment of the present invention includes a polypeptide having an amino acid sequence represented by the following General Formula 1.

[General Formula 1]
(SEQ ID NOs. 7-9)
R1-X1-QGTFTSDYSKYLD-R2-EFVQWLMNT-R3, wherein R1 is histidine, desamino-histidyl, N-dimethylhistidyl, beta-hydroxy-imidazo-propionyl, 4-imidazoacetyl, or beta-carboxy-imidazo-propionyl; X1 is a deletion, glycine, or aminoisobutyric acid (Aib); R2 is EKRAK (SEQ ID NO. 10), EQAAK (SEQ ID NO. 11), or EEAVK (SEQ ID NO. 12); and R3 is a deletion, cysteine, lysine, or methionine.

The polypeptide may be covalently bound to, or may form microspheres with any one or more selected from the group consisting of a non-peptidic polymer, a fatty acid, cholesterol, an antibody, an antibody fragment, albumin and a fragment thereof, a nucleotide, fibronectin, transferrin, an FcRn-binding material, a saccharide, elastin, heparin, and derivatives thereof.

R2 includes glutamic acid (E) and lysine (K), and the glutamic acid and the lysine may be taken together to form a ring via an amide bond, which may contribute to an alpha helix structure of the polypeptide.

The non-peptidic polymer may be selected from the group consisting of polyethylene glycol (PEG), polypropylene glycol, a copolymer of ethylene glycol and propylene glycol, polyoxyethylated polyol, polyvinyl alcohol (PVA), a polysaccharide, dextran, polyvinyl ethyl ether, polylactic acid (PLA), polylactic-glycolic acid (PLGA), a lipid polymer, chitin, hyaluronic acid, and a combination thereof. The derivatives of the non-peptidic polymer known in the related art, and other derivatives that may be easily prepared at the technical level of the prior art also fall within the scope of the present invention.

Preferably, the non-peptidic polymer may be polyethylene glycol or a derivative thereof.

The non-peptidic polymer may have a molecular weight of 3,000 to 100,000 Da.

In this case, the polyethylene glycol derivative may be at least one selected from the group consisting of methoxypolyethylene glycol, methoxypolyethylene glycol N-hydroxysuccinimide, methoxypolyethylene glycol propionaldehyde, methoxypolyethylene glycol maleimide, polyethylene glycol succinimidyl propionate (PEG succinimidyl propionate), methoxy polyethylene glycol succinimidyl propionate (methoxy PEG succinimidyl propionate), acrylate polyethylene glycol succinimidyl propionate (acrylate PEG succinimidyl propionate), thiol polyethylene glycol succinimidyl propionate (thiol PEG succinimidyl propionate), hydroxy succinimidyl polyethylene glycol (hydroxy succinimidyl PEG), methoxypolyethylene glycol succinimidyl carboxymethyl ester (mPEG succinimidyl carboxymethyl ester), acrylate polyethylene glycol succinimidyl carboxymethyl ester (acrylate PEG succinimidyl carboxymethyl ester), polyethylene glycol succinimidyl carbonate (PEG succinimidyl carbonate), polyethylene glycol propionaldehyde (PEG propionaldehyde), polyethylene glycol butyl aldehyde (PEG butyl aldehyde), derivatives thereof, and multi-branched forms of derivatives thereof.

The polyethylene glycol or the derivative thereof may be linear or branched.

The pharmaceutical composition may be used to prevent or treat one or more diseases selected from the group consisting of obesity, diabetes, and non-alcoholic fatty liver disease.

The non-alcoholic fatty liver disease may include one or more diseases selected from the group consisting of non-alcoholic fatty liver, non-alcoholic steatohepatitis, liver cirrhosis, and liver cancer.

A method of preparing a pharmaceutical composition according to another exemplary embodiment of the present invention includes mixing a non-peptidic polymer with a polypeptide having an amino acid sequence represented by the following General Formula 1 to react with each other.

[General Formula 1]
(SEQ ID NOs. 7-9)
R1-X1-QGTFTSDYSKYLD-R2-EFVQWLMNT-R3, wherein R1 is histidine, desamino-histidyl, N-dimethylhistidyl, beta-hydroxy-imidazo-propionyl, 4-imidazoacetyl, or beta-carboxy-imidazo-propionyl; X1 is a deletion, glycine, or aminoisobutyric acid (Aib); R2 is EKRAK (SEQ ID NO. 10), EQAAK (SEQ ID NO. 11), or EEAVK (SEQ ID NO. 12); and R3 is a deletion, cysteine, lysine, or methionine.

The non-peptidic polymer may be selected from the group consisting of polyethylene glycol (PEG), polypropylene glycol, a copolymer of ethylene glycol and propylene glycol, polyoxyethylated polyol, polyvinyl alcohol (PVA), a polysaccharide, dextran, polyvinyl ethyl ether, polylactic acid (PLA), polylactic-glycolic acid (PLGA), a lipid polymer, chitin, hyaluronic acid, and a combination thereof. The derivatives of the non-peptidic polymer known in the related art, and other derivatives that may be easily prepared at the technical level of the prior art also fall within the scope of the present invention.

Preferably, the non-peptidic polymer may be polyethylene glycol or a derivative thereof.

In this case, the polyethylene glycol derivative may be at least one selected from the group consisting of methoxypolyethylene glycol, methoxypolyethylene glycol N-hydroxysuccinimide, methoxypolyethylene glycol propionaldehyde, methoxypolyethylene glycol maleimide, polyethylene glycol succinimidyl propionate (PEG succinimidyl propionate), methoxy polyethylene glycol succinimidyl propionate (methoxy PEG succinimidyl propionate), acrylate polyethylene glycol succinimidyl propionate (acrylate PEG succinimidyl propionate), thiol polyethylene glycol succinimidyl propionate (thiol PEG succinimidyl propionate), hydroxy succinimidyl polyethylene glycol (hydroxy succinimidyl PEG), methoxypolyethylene glycol succinimidyl carboxymethyl ester (mPEG succinimidyl carboxymethyl ester), acrylate polyethylene glycol succinimidyl carboxymethyl ester (acrylate PEG succinimidyl carboxymethyl ester), polyethylene glycol succinimidyl carbonate (PEG succinimidyl carbonate), polyethylene glycol propionaldehyde (PEG propionaldehyde), polyethylene glycol butyl aldehyde (PEG butyl aldehyde), derivatives thereof, and multi-branched forms of derivatives thereof.

The mixing of the non-peptidic polymer with the polypeptide to react each other may include allowing the polypeptide and the non-peptidic polymer to react at a molar ratio of 1:1 to 1:5.

The mixing of the non-peptidic polymer with the polypeptide to react each other may be performed at pH 4.0 to 9.0.

In the mixing of the non-peptidic polymer with the polypeptide to react each other, the reaction time may be in a range of 0.5 to 24 hours.

The pharmaceutical composition may be used to prevent or treat one or more diseases selected from the group consisting of obesity, diabetes, and non-alcoholic fatty liver disease.

The non-alcoholic fatty liver disease may include one or more diseases selected from the group consisting of non-alcoholic fatty liver, non-alcoholic steatohepatitis, liver cirrhosis, and liver cancer.

A method of preventing or treating one or more diseases selected from the group consisting of obesity, diabetes, and non-alcoholic fatty liver disease according to another exemplary embodiment of the present invention includes administering the pharmaceutical composition to a subject.

Advantageous Effects of Invention

The pharmaceutical composition according to the present invention can include the polypeptide, and thus have effects of reducing food intake, enhancing insulin secretion, suppressing gastric emptying, promoting lipolysis, and lowering a level of triglycerides.

Also, the pharmaceutical composition according to the present invention can include the polypeptide, and thus can reduce side effects such as vomiting or nausea, and the like.

Additionally, the pharmaceutical composition according to the present invention can include a non-peptidic polymer which is highly selective and reactive with the polypeptide, and thus can be prepared in high yield.

Further, the pharmaceutical composition according to the present invention can include a conjugate including the polypeptide and the non-peptidic polymer, and thus can have a long in vivo half-life, and a high therapeutic effect on obesity even when administered at a low dose, and also can have effects of lowering a blood glucose level so that the blood glucose can be maintained at a normal level, and effectively lowering a triglyceride level.

BRIEF DESCRIPTION OF DRAWINGS

FIG. 1 shows the HPLC results of a conjugate of Example 2 including a polypeptide and a non-peptidic polymer.

FIG. 2 shows the MALDI-TOF results of the conjugate of Example 2 including the polypeptide and the non-peptidic polymer.

FIG. 3 shows the results of measuring a level of glycated hemoglobin (HbA1c) after the end of treatment with the conjugate of Example 2 in order to determine a degree of change in a long-term average blood glucose concentration (**$p<0.01$).

FIG. 4 shows the results of the final body weights of mice after the treatment with conjugate of Example 2 for two weeks with different dosing frequency (***$p<0.001$).

FIG. 5 shows the results of changes in blood glucose in the mice after the administration of conjugate of Example 2 or 6.

FIG. 6 shows the results of an intraperitoneal glucose tolerance test (ipGTT) after the administration of conjugate of Example 2 or 6.

FIG. 7 shows the results of measuring changes in serum cholesterol after the administration of the conjugate of Example 2.

FIG. 8 shows the results of measuring changes in weights of the livers after the administration of the conjugate of Example 2.

FIG. 9 shows the results of observing liver tissues of mice after the administration of the conjugate of Example 2 (a darkly stained region represents a normal liver tissue, and a white (brilliantly)-stained region represents a lipid droplet).

FIG. 10 shows the results of measuring changes in serum cholesterol after the administration of the conjugate of Example 2.

FIG. 11 shows the results of measuring changes in weights of the livers after the administration of the conjugate of Example 2.

FIG. 12 shows the results of measuring changes in levels of hepatic triglycerides after the administration of the conjugate of Example 2.

FIG. 13 shows the results of observing liver tissues of mice after the administration of the conjugate of Example 2 (a darkly stained region represents a normal liver tissue, and a white (brilliantly)-stained region represents a lipid droplet).

FIG. 14 shows the results of measuring NAFLD activity scores (NAS) after the administration of the conjugate of Example 2.

BEST MODE FOR CARRYING OUT THE INVENTION

The present invention provides a polypeptide having an amino acid sequence represented by the following General Formula 1.

[General Formula 1]
(SEQ ID NOs. 7-9)
R1-X1-QGTFTSDYSKYLD-R2-EFVQWLMNT-R3, wherein R1 is histidine, desamino-histidyl, N-dimethyl-histidyl, beta-hydroxy-imidazo-propionyl, 4-imidazoacetyl, or beta-carboxy-imidazo-propionyl;

X1 is a deletion, glycine, or aminoisobutyric acid (Aib);

R2 is EKRAK (SEQ ID NO. 10), EQAAK (SEQ ID NO. 11), or EEAVK (SEQ ID NO. 12); and R3 is a deletion, cysteine, lysine, or methionine.

The present invention provides a polypeptide having an amino acid sequence represented by the following General Formula 1 for use in a prevention or a treatment of disease selected from the group consisting of obesity, diabetes, and non-alcoholic fatty liver disease.

[General Formula 1]
(SEQ ID NOs. 7-9)
R1-X1-QGTFTSDYSKYLD-R2-EFVQWLMNT-R3, wherein R1 is histidine, desamino-histidyl, N-dimethyl-histidyl, beta-hydroxy-imidazo-propionyl, 4-imidazoacetyl, or beta-carboxy-imidazo-propionyl;

X1 is a deletion, glycine, or aminoisobutyric acid (Aib);

R2 is EKRAK (SEQ ID NO. 10), EQAAK (SEQ ID NO. 11), or EEAVK (SEQ ID NO. 12); and R3 is a deletion, cysteine, lysine, or methionine.

The present invention provides a pharmaceutical composition, which includes a polypeptide having an amino acid sequence represented by the following General Formula 1.

[General Formula 1]
(SEQ ID NOs. 7-9)
R1-X1-QGTFTSDYSKYLD-R2-EFVQWLMNT-R3, wherein R1 is histidine, desamino-histidyl, N-dimethyl-histidyl, beta-hydroxy-imidazo-propionyl, 4-imidazoacetyl, or beta-carboxy-imidazo-propionyl;

X1 is a deletion, glycine, or aminoisobutyric acid (Aib);

R2 is EKRAK (SEQ ID NO. 10), EQAAK (SEQ ID NO. 11), or EEAVK (SEQ ID NO. 12); and R3 is a deletion, cysteine, lysine, or methionine.

The present invention provides a pharmaceutical composition comprising a polypeptide having an amino acid sequence represented by the General Formula 1 above for preventing or treating disease selected from the group consisting of obesity, diabetes, and non-alcoholic fatty liver disease.

Amino acids mentioned herein are abbreviated according to the IUPAC-IUB nomenclature rules, as listed in the following Table 1.

TABLE 1

| Amino acids | Abbreviations | Amino acids | Abbreviations |
|---|---|---|---|
| Alanine | A | Arginine | R |
| Asparagine | N | Aspartic acid | D |
| Cysteine | C | Glutamic acid | E |
| Glutamine | Q | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

In General Formula 1, R1 is preferably histidine at the N-terminus of the polypeptide, but the present invention is not limited thereto.

X1 is preferably glycine or Aib, more preferably Aib. In this case, X1 is not particularly limited as long as it can enhance the chemical stability of the polypeptide.

Also, X1 is preferred as long as it can have resistance to dipeptidyl peptidase-4 (DPP-4), thereby enhancing the enzyme stability.

R2 is preferably EQAAK (SEQ ID NO. 11) or EEAVK (SEQ ID NO. 12), more preferably EQAAK (SEQ ID NO. 11), but the present invention is not limited thereto.

R2 includes glutamic acid (E) and lysine (K), and the glutamic acid and the lysine are preferably taken together to form a ring via an amide bond, but the present invention is not limited thereto. As such, when two residues in the amino acid sequence of the polypeptide form a covalent ring via an amide bond, the covalent ring may enhance the in vivo stability, and improve an ability of binding to a glucagon receptor or a glucagon derivative receptor. Also, the covalent ring may contribute to an alpha helix structure of the polypeptide.

R3 is the C-terminus of the polypeptide that may bind to a substance in order to enhance the in vivo half-life or in vivo sustainability. In this case, R3 is preferably cysteine, but the present invention is not limited thereto.

The polypeptide may have 70% to 90% sequence homology to the amino acid sequence set forth in SEQ ID NO. 1 (SEQ ID NO. 1: HSQGTFTSDYSKYLDSR-RAQDFVQWLMNT).

Here, it is reported that the amino acid sequence set forth in SEQ ID NO. 1 is identical to some or all of an amino acid sequence of natural glucagon, and the natural glucagon promotes the degradation of glycogen and insulin and exhibits an anti-obesity effect. However, the use of the natural glucagon as a therapeutic agent is limited due to the low solubility and its precipitation at the neutral pH.

That is, the polypeptide including the amino acid sequence having 70% to 90% sequence homology to the amino acid sequence set forth in SEQ ID NO. 1 may be a glucagon derivative or an oxyntomodulin derivative. In this case, the oxyntomodulin derivative is a peptide that is made from a glucagon precursor (e.g., pre-glucagon).

Preferably, the polypeptide may have 73% to 90%, more preferably 75% to 90% sequence homology to the amino acid sequence set forth in SEQ ID NO. 1, but the present invention is not limited thereto.

In this specification, the term "homology" refers to a degree of similarity to a wildtype amino acid sequence and a wild-type nucleic acid sequence. In this case, the comparison of homology between these sequences is performed using an available comparison program. A commercially available computer program may be used to calculate the homology between two or more sequences as a percentage (%). The homology (%) may be calculated for adjacent sequences. A large amount of the peptide may be secured by inserting a polynucleotide encoding the peptide into a vector and expressing the peptide.

In this specification, the term "peptide" refers to a compound in which two or more α-amino acids are linked via a peptide bond.

Meanwhile, the polypeptide may be covalently bound to, or may form microspheres with any one or more selected from the group consisting of a non-peptidic polymer, a fatty acid, cholesterol, an antibody, an antibody fragment, albumin and a fragment thereof, a nucleotide, fibronectin, transferrin, an FcRn-binding material, a saccharide, elastin, heparin, and derivatives thereof.

Preferably, the non-peptidic polymer is covalently bound to the polypeptide, but the present invention is not limited thereto.

The polypeptide is covalently bound to, or forms microspheres with the aforementioned substances, and thus has effects of enhancing the blood stability, delaying the drug release into the kidney, and inducing a change in affinity to receptors.

The polypeptide may enhance the in vivo half-life and extend an in vivo retention time when the polypeptide is covalently bound to the non-peptidic polymer. In this case, a binding site between the non-peptidic polymer and the polypeptide may vary depending on the functional group of the non-peptidic polymer and the amino acid sequence of the polypeptide. Preferably, the binding site is not particularly limited as long as the non-peptidic polymer is polymerized to the C-terminus of the polypeptide, or it can be prepared in high yield due to a high reaction rate.

When the non-peptidic polymer is bound to the polypeptide, a non-peptidic polymer having a maleimide group may bind to the polypeptide using a sulfhydryl (—SH) group of the C-terminal cysteine of the polypeptide, or a non-peptidic polymer having a succinimide derivative may bind to the polypeptide using an amine group of lysine (K) of the polypeptide.

The non-peptidic polymer may be selected from the group consisting of polyethylene glycol (PEG), polypropylene glycol, a copolymer of ethylene glycol and propylene glycol, polyoxyethylated polyol, polyvinyl alcohol (PVA), a polysaccharide, dextran, polyvinyl ethyl ether, polylactic acid (PLA), polylactic-glycolic acid (PLGA), a lipid polymer, chitin, hyaluronic acid, and a combination thereof. Preferably, the non-peptidic polymer is polyethylene glycol or a derivative thereof, but the present invention is not limited thereto. The derivatives of the non-peptidic polymer known in the related art, and other derivatives that may be easily prepared at the technical level of the prior art also fall within the scope of the present invention.

The polyethylene glycol derivative may be at least one selected from the group consisting of methoxypolyethylene glycol, methoxypolyethylene glycol N-hydroxysuccinimide, methoxypolyethylene glycol propionaldehyde, methoxypolyethylene glycol maleimide, polyethylene glycol succinimidyl propionate (PEG succinimidyl propionate), methoxy polyethylene glycol succinimidyl propionate (methoxy PEG succinimidyl propionate), acrylate polyethylene glycol succinimidyl propionate (acrylate PEG succinimidyl propionate), thiol polyethylene glycol succinimidyl propionate (thiol PEG succinimidyl propionate), hydroxy succinimidyl polyethylene glycol (hydroxy succinimidyl PEG), methoxypolyethylene glycol succinimidyl carboxymethyl ester (mPEG succinimidyl carboxymethyl ester), acrylate polyethylene glycol succinimidyl carboxymethyl ester (acrylate PEG succinimidyl carboxymethyl ester), polyethylene glycol succinimidyl carbonate (PEG succinimidyl carbonate), polyethylene glycol propionaldehyde (PEG propionaldehyde), polyethylene glycol butyl aldehyde (PEG butyl aldehyde), derivatives thereof, and multi-branched forms of derivatives thereof. Preferably, the polyethylene glycol derivative is linear methoxypolyethylene glycol maleimide, di-branched methoxypolyethylene glycol maleimide, or tri-branched methoxypolyethylene glycol maleimide, more preferably tri-branched methoxy polyethylene glycol maleimide.

The polyethylene glycol or the derivative thereof that may be used herein is linear or branched, preferably di-branched or tri-branched, and more preferably tri-branched.

The non-peptidic polymer may have a molecular weight of 3,000 to 100,000 Da, preferably 20,000 to 70,000 Da, and more preferably 40,000 to 60,000 Da. When the non-peptidic polymer has a molecular weight within this molecular weight range, the non-peptidic polymer may bind to the polypeptide to enhance the solubility of the resulting conjugate and extend an in vivo retention time of the conjugate.

Therefore, the pharmaceutical composition according to the present invention includes a conjugate having a non-peptidic polymer bound to the polypeptide, and thus may enhance the in vivo stability and extend the in vivo half-life.

Also, the pharmaceutical composition according to the present invention includes the conjugate including the polypeptide or including the polypeptide and the non-peptidic polymer, and thus may be used in the pharmaceutical composition for the purpose of preventing or treating one or more diseases selected from the group consisting of obesity, diabetes, and non-alcoholic fatty liver disease.

Also, the pharmaceutical composition including the conjugate, which includes the polypeptide or includes the polypeptide and the non-peptidic polymer, according to the present invention may be used in the pharmaceutical composition for the purpose of preventing or treating diseases caused due to a deficiency of insulin secretion or a reduced insulin sensitivity.

The diseases caused due to the deficiency of insulin secretion or the reduced insulin sensitivity may include type I diabetes, type II diabetes, and diabetic complications.

Also, the pharmaceutical composition including the conjugate, which includes the polypeptide or includes the polypeptide and the non-peptidic polymer, according to the present invention may be used as the pharmaceutical composition for the purpose of preventing, improving, or treating diseases such as hyperlipidemia, cardiovascular diseases, arteriosclerosis, and lipid-related metabolic syndromes.

Also, the pharmaceutical composition including the conjugate, which includes the polypeptide or includes the polypeptide and the non-peptidic polymer, according to the present invention may be used as the pharmaceutical composition for the purpose of preventing, improving, or treating liver diseases such as liver cancer, liver cirrhosis, non-alcoholic steatohepatitis, and non-alcoholic fatty liver.

When the composition of the present invention is used as a medicine, the pharmaceutical composition including the polypeptide may be formulated into the following various dosage forms for oral or parenteral administration, which are then clinically administered, but the present invention is not limited thereto.

Formulations for oral administration include, for example, tablets, pills, hard/soft capsules, solutions, suspensions, emulsions, syrups, granules, elixirs, troches, and the like. In addition to the active ingredient, these formulations contain diluents (e.g., lactose, dextrose, sucrose, mannitol, sorbitol, cellulose, and/or glycine), lubricants (e.g., silica, talc, stearic acid and magnesium or calcium salts thereof, and/or polyethylene glycol). The tablets may also contain a binding agent such as magnesium aluminum silicate, starch paste, gelatin, methylcellulose, sodium carboxymethylcellulose, and/or polyvinylpyrrolidine, and may optionally contain a disintegrating agent such as starch, agar, alginic acid or sodium salts thereof, or an effervescent mixture, and/or an absorbent, a coloring agent, a flavoring agent, and a sweetening agent.

The pharmaceutical composition including the polypeptide may be administered parenterally. In this case, the parenteral administration is made by means of methods such as subcutaneous, intravenous, intramuscular injections, intranasal spray, administration into the nasal cavity or intestines via a mucous membrane, administration by inhalation, or intrathoracic injection.

In this case, to allow for preparation into formulations for parenteral administration, the polypeptide may be mixed with a stabilizing agent or a buffer to prepare a solution or a suspension, which may be prepared into unit dosage forms for ampoules or vials. The composition may be sterile and/or contain adjuvants such as a preservative, a stabilizing agent, a wetting agent or an emulsion promoter, a salt and/or buffer for osmotic regulation, and other therapeutically useful substances. In this case, the composition may be formulated according to conventional methods such as mixing, granulation, or coating methods.

An amount of the pharmaceutical composition including the polypeptide according to the present invention to be administered into the human body may vary depending on the age, weight, sex, a mode of administration, health condition, and the severity of a disease of a patient. For example, the pharmaceutical composition may be administered through a route of oral or parenteral administration at a dose of 0.001 to 200 mg/kg/day according to the doctors' or pharmacists' judgments.

Also, the present invention provides a method of preparing a pharmaceutical composition including a conjugate, which includes a polypeptide and a non-peptidic polymer.

First of all, in the method of preparing a pharmaceutical composition, the polypeptide has an amino acid sequence represented by General Formula 1 as described above. Also, the non-peptidic polymer is as described above, and thus detailed description of the polypeptide and the non-peptidic polymer will be omitted.

Specifically, the method of preparing a pharmaceutical composition includes mixing a non-peptidic polymer with a polypeptide to react with each other. In this case, the polypeptide and the non-peptidic polymer may react at a molar ratio of 1:1 to 1:5 so that the polypeptide and the non-peptidic polymer can bind to each other at a molar ratio of 1:1. In this case, the mixing is preferably performed at a molar ratio of 1:1 to 1:2, and more preferably a molar ratio of 1:1.2, but the present invention is not limited thereto. When the mixing is performed within this molar ratio range, a conjugate may be obtained in high yield, which makes it possible to prepare a high-purity conjugate including polypeptide and non-peptidic polymer.

According to one exemplary embodiment of the present invention, a conjugate may also be prepared by covalently linking the non-peptidic polymer to the C-terminus of the polypeptide. For example, the conjugate may also be prepared with high reactivity using, as the non-peptidic polymer, methoxypolyethylene glycol having a maleimide group, and, as the polypeptide, a polypeptide having cysteine at the C-terminus thereof, and thus may have a high yield and extend the blood half-life.

The mixing of the non-peptidic polymer with the polypeptide to react with each other may be performed at pH 4.0 to 9.0, preferably pH 5.5 to 7.5, but the present invention is not limited thereto. When the mixing is performed out of this pH range, the yield will be lowered. For example, when methoxypolyethylene glycol having a maleimide group is used as the non-peptidic polymer, and a polypeptide having cysteine at the C-terminus thereof is used as the polypeptide, the mixing is preferably performed at pH 6 to 8. When the polypeptide and the methoxypolyethylene glycol are reacted within this pH range, side reactions such as a ring opening phenomenon for maleimide can be suppressed without causing side reactions by the amine group of the polypeptide.

Because the conjugate has a yield of 85 to 95% in the mixing of the non-peptidic polymer with the polypeptide to react with each other, the process will be economically feasible due to the very high yield, and be highly reproducible. Therefore, the process will be effectively used to prepare medicines.

In the mixing of the non-peptidic polymer with the polypeptide to react with each other, the reaction time may be in a range of 0.5 to 24 hours, or 1 to 24 hours, and preferably 2 hours, but the present invention is not limited thereto. When the reaction time is less than 0.5 hours, the yield will be lowered, and the purity will be decreased. On the other hand, when the reaction time exceeds 24 hours, the polypeptide may be degraded, or the economic effects may be declined due to the long processing time.

Also, in the mixing of the non-peptidic polymer with the polypeptide to react with each other, the temperature may be in a range of 0 to 100° C., preferably 4 to 40° C., but the present invention is not limited thereto. Also, the temperature is not particularly limited as long as there is no chemical change in the polypeptide or non-peptidic polymer.

In the mixing of the non-peptidic polymer with the polypeptide to react with each other, each of the polypeptide and the non-peptidic polymer may be dissolved using the same or different solvents. Preferably, the solvent is a buffering solution, an alcohol, dimethyl sulfoxide (DMSO), or a mixture thereof, but the present invention is not limited thereto. Also, the solvent includes solvents that may be readily used in the related art.

The present invention provides a method of preventing or treating one or more diseases selected from the group consisting of obesity, diabetes, and non-alcoholic fatty liver disease, which includes administering the pharmaceutical composition including the polypeptide to a subject.

Also, the present invention provides a method of preventing or treating one or more diseases selected from the group consisting of obesity, diabetes, and non-alcoholic fatty liver disease, which includes administering the pharmaceutical composition including the polypeptide to a subject other than a human being.

MODE FOR THE INVENTION

Herein after, the present invention will be described in detail with reference to the accompanying drawings so that a person having ordinary knowledge in the art to which the present invention belongs can easily put the invention into practice. However, it should be understood that the present invention may be embodied in various forms, but is not intended to be limiting in this context. Throughout the specification, like reference numerals refer to like elements.

Example 1

A polypeptide, into which cysteine was introduced (molecular weight: 3,509 Da;

```
SEQ ID NO. 2:
H(Aib)QGTFTSDYSKYLDEQAAKEFVQWLMNTC).
```

Here, the residues underlined and highlighted in bold in the amino acid sequence of SEQ ID NO. 2 represents that a covalent ring is formed between the residues.

Preparative Example 1: Synthesis of Conjugate Including Polypeptide and Non-Peptidic Polymer To prepare a conjugate including a polypeptide and a non-peptidic polymer, a polypeptide in which cysteine was introduced into the C-terminal region (at position 30) (molecular weight: 3,509 Da;

```
SEQ ID NO. 2:
H(Aib)QGTFTSDYSKYLDEQAAKEFVQWLMNTC)
``` was used as the polypeptide.

Meanwhile, maleimide-activated monomethoxy PEG (mPEG-MAL, NOF (Japan)) was used as the non-peptidic polymer, as listed in the following Table 2.

To prepare conjugates of Examples 2 to 7, the polypeptides were prepared as listed in the following Table 2. In this case, each of the polypeptides was dissolved in dimethyl sulfoxide (DMSO), and the mPEG-MAL was dissolved in 50 mM phosphate buffer saline (pH 6).

TABLE 2

| Items | Polypeptides | Non-peptidic polymers |
|---|---|---|
| Example 2 | Polypeptide having an amino acid sequence of H(Aib)QGTFTSDYSKYLDEQAAKEFVQWLMNTC (SEQ ID NO. 2) | Tri-branched mpeg-MAL (MW: 50 kDa) |
| Example 3 | Polypeptide having an amino acid sequence of H(Aib)QGTFTSDYSKYLDEQAAKEFVQWLMNTC (SEQ ID NO. 2) | Di-branched mpeg-MAL (MW: 20 kDa) |
| Example 4 | Polypeptide having an amino acid sequence of H(Aib)QGTFTSDYSKYLDEQAAKEFVQWLMNTC (SEQ ID NO. 2) | Linear mpeg-MAL (MW: 20 kDa) |
| Example 5 | Polypeptide having an amino acid sequence of HGQGTFTSDYSKYLDEKRAKEFVQWLMNTC (SEQ ID NO. 3) | Tri-branched mpeg-MAL (MW: 50 kDa) |
| Example 6 | Polypeptide having an amino acid sequence of H(Aib)QGTFTSDYSKYLDEEAVKEFVQWLMNTC (SEQ ID NO. 4) | Tri-branched mpeg-MAL (MW: 50 kDa) |
| Example 7 | Polypeptide having an amino acid sequence of HGQGTFTSDYSKYLDEEAVKEFVQWLMNTC (SEQ ID NO. 5) | Tri-branched mpeg-MAL (MW: 50 kDa) |

In the amino acid sequences of SEQ ID NOS. 2 to 4 as listed in Table 2, the two residues underlined and highlighted in bold refer to residues having a covalent ring formed therebetween.

The polypeptide and the non-peptidic conjugate were mixed in a molar ratio of 1:1.2, and reacted at room temperature for 2 hours. After the reaction was completed, the reaction solution was separated by ion exchange chromatography using a TSK SP-5PW column (7.5 T 75 mm, Tosoh, Japan) at a flow rate of 0.8 mL/min. The separation was monitored at a UV wavelength of 280 nm. A PEGylated polypeptide was separated using a linear gradient method using a 20 mM acetate buffer solution (pH 4) (mobile phase A) and a 1 M sodium chloride solution (in a 20 mM acetate buffer solution (pH 4)) (mobile phase B) as mobile phases. HPLC was performed to evaluate the purity of the PEGylated polypeptide (see FIG. 1). Next, a molecular weight of the PEGylated polypeptide was measured using a MALDI-TOF mass spectrometer (see FIG. 2). Also, from the chromatogram obtained during a chromatographic separation process, the yields of the conjugates of Examples 2 to 7 were calculated as the area ratios of the conjugates with respect to the polypeptide. The results are listed in Table 3.

TABLE 3

| Items | Yield |
|---|---|
| Example 2 | 90% |
| Example 3 | 92% |
| Example 4 | 91% |
| Example 5 | 89% |
| Example 6 | 91% |
| Example 7 | 90% |

As listed in Table 3, it was confirmed that the conjugates were prepared at a yield of 90% or more. Therefore, the method of preparing a pharmaceutical composition according to the present invention has an advantage in that the method can be effectively used to prepare therapeutic agent because the conjugates are obtained with high yield due to the high reactivity with the peptides, and the method is economically feasible and highly reproducible due to a simple preparation process.

Experimental Example 1: Measurement of In Vitro Activity of Example 2

To check a prophylactic or therapeutic effect of the conjugate of Example 2 on obesity, diabetes, and non-alcoholic fatty liver disease, this experiment was performed using a cell line expressing a GLP-1 (glucagon derivative) receptor and a glucagon receptor (GCGR).

To determine the activity on the GLP-1 receptor, HEK293/CRE-Luc cells expressing a human glucagon GLP-1 receptor were purchased from GenScript and used. The cells were seeded in a 96-well plate at $5\times10^4$ cells/well, and each of the wells was then treated with the polypeptide of Example 1 (0.001 to 300 nM), the conjugate of Example 2 (0.001 to 300 nM), natural glucagon (SEQ ID NO. 1: HSQGTFTSDYSKYLDSRRAQDFVQWLMNT, 0.013 to 300 nM), and GLP-1 (SEQ ID NO. 6: HAEGTFTSDVS- SYLEGQAAKEFIAWLVKGR, 0.001 to 300 nM). Thereafter, the cells were incubated for 4 hours under conditions of a temperature of 37° C. in a $CO_2$ incubator. Subsequently, an amount of the generated cAMP (a luciferase reporter) was measured using a One-Glo™ Luciferase assay system (Promega) to calculate an $EC_{50}$ value with respect to the GLP-1 receptor. The results are listed in the following Table 4.

Second, to determine the activity on the glucagon receptor (GCGR), a cAMP Hunter™ eXpress GCGR CHO-K1 GPCR assay kit from the company DiscoverX was used. CHO-K1 cells expressing a human glucagon receptor were used and seeded in a 96-well plate at a density of $3 \times 10^4$ cells/well. Thereafter, each of the wells was treated with the polypeptide of Example 1 (0.013 to 300 nM), the conjugate of Example 2 (0.013 to 300 nM), natural glucagon (0.015 to 33.33 nM), and GLP-1 (0.001 to 30.00 nM), and the cells were than incubated for 30 minutes under conditions of a temperature of 37° C. in a $CO_2$ incubator. Then, an amount of the generated cAMP was measured to calculate an $EC_{50}$ value with respect to the glucagon receptor (GCGR). The results are listed in the following Table 4.

TABLE 4

| Items | $EC_{50}$ of GLP-1 receptor (nM) | $EC_{50}$ of glucagon receptor (GCGR) (nM) |
|---|---|---|
| Example 1 | 0.13 | 38.65 |
| Example 2 | 2.12 | 46.98 |
| Natural glucagon | 11.42 | 0.15 |
| GLP-1 | 0.07 | >1,000 |

As listed in Table 4, GLP-1 exhibited high activity on the GLP-1 receptor, but had very low activity on the glucagon receptor, which was not measurable. On the other hand, the natural glucagon had very high activity on the glucagon receptor, but exhibited low activity on the GLP-1 receptor. Based on these results, it was confirmed that the experimental method had high selectivity.

Meanwhile, it was confirmed that the polypeptide of Example 1 had an $EC_{50}$ value of 0.13 on the GLP-1 receptor, the value of which was nearly identical to that of GLP-1, indicating that the polypeptide of Example 1 exhibited very high activity on the GLP-1 receptor, and that the polypeptide of Example 1 also had activity on the glucagon receptor. Also, it was confirmed that the polypeptide of Example 1 had an anti-obesity effect using an animal experiment.

Also, it was confirmed that the conjugate of Example 2 retained similar activity on the GLP-1 receptor and the glucagon receptor, compared to the polypeptide of Example 1. It was confirmed that the polypeptide generally had significantly reduced activity on the receptors when the non-peptidic polymer (e.g. PEG) was bound to the polypeptide, compared to before the conjugation, whereas the conjugate of Example 2 had less reduced activity on the receptors even when the non-peptidic polymer was bound to the polypeptide, indicating that the conjugate of Example 2 exhibited an extended in vivo half-life while maintaining the high activity.

Therefore, it was confirmed that the pharmaceutical composition according to the present invention had excellent activity on the glucagon receptor and the GLP-1 receptor, and thus had anti-diabetic and anti-obesity effects as well as a triglyceride-lowering effect by suppressing the appetite, enhancing the insulin secretion, and promoting the lipolysis in fat cells.

Experimental Example 2: Measurement 1 of In Vivo Activity of Example 2

To check a preventing or therapeutic effect of the conjugate of Example 2 on obesity or diabetes, the conjugate of Example 2 was administered to C57BL/6 mice to measure changes in food intake, blood glucose, and body weights. The results are listed in Table 5.

First, an obesity animal model was prepared by feeding a 60% high-fat diet to normal C57BL/6 mice (approximately 6 weeks old) for approximately 24 weeks, and increasing the body weights of the mice to approximately 50 g on average. Thereafter, the conjugate of Example 2 was administered by subcutaneous injection at a dose of 20 nmol/kg once every other day for 2 weeks. As the positive control, a GLP-1 agonist 'liraglutide' was also administered by subcutaneous injection at a dose of 100 nmol/kg once a day for 2 weeks. For 2 weeks when the drug was administered, the food intake, the blood glucose, and the body weights were measured once every other day at given points of time. The results are listed in the following Table 5.

In this case, the body weights and the blood glucose were expressed in the percentage (%) on the basis of 100% before the administration (Day 0).

TABLE 5

| | Example 2 | | | Positive control | | | Non-treated group | | |
|---|---|---|---|---|---|---|---|---|---|
| Time (day) | Body weight (%) | Food intake (g) | Blood glucose (%) | Body weight (%) | Food intake (g) | Blood glucose (%) | Body weight (%) | Food intake (g) | Blood glucose (%) |
| 0 | 100 | 0 | 100 | 100 | 0 | 100 | 100 | 0 | 100 |
| 2 | 97 | 4 | 87 | 93 | 2 | 59 | 100 | 6 | 93 |
| 4 | 94 | 8 | 75 | 92 | 5 | 78 | 101 | 11 | 125 |
| 6 | 89 | 11 | 48 | 90 | 9 | 80 | 100 | 16 | 123 |
| 8 | 82 | 13 | 32 | 89 | 13 | 81 | 101 | 21 | 110 |
| 10 | 74 | 15 | 35 | 87 | 16 | 85 | 102 | 28 | 129 |
| 12 | 68 | 17 | 32 | 86 | 19 | 88 | 102 | 34 | 120 |
| 14 | 61 | 18 | 18 | 86 | 22 | 93 | 102 | 40 | 121 |

In this case, a non-treated group refers to a group of mice to which PBS is administered instead of the conjugate of Example 2.

As listed in Table 5, the non-treated group ate approximately 40 g of food for 2 weeks, whereas a group of mice to which the conjugate of Example 2 was administered ate approximately 18 g of food, the cumulative food intake of which was reduced by more than half, compared to that of the non-treated group. The food intakes were similar in the groups of mice to which the positive control and the conjugate of Example 2 were administered.

Meanwhile, referring to the pattern of changes in body weights with time, the changes in body weights were not observed in the non-treated group, compared to those observed at a point of time of administration (Day 0), and the body weights were reduced by approximately 15% in the positive control, compared to those observed before the administration, indicating that the liraglutide had a poor preventing or therapeutic effect on obesity. On the other hand, in the group of mice to which the conjugate of Example 2 was administered, the body weights were remarkably lost to 61%, compared to those measured before the administration.

Also, referring to the pattern of changes in blood glucose with time, it was revealed that a level of blood glucose was reduced by approximately 80%, compared to those measured before the administration, indicating that the conjugate of Example 2 had an effect of lowering a level of blood glucose, but that the positive control had a poor blood glucose-lowering effect.

Based on these results, it can be seen that an effect of the conjugate of Example 2 on the body weight loss was an effect exerted by an increase in energy metabolism in the body as well as a simple decrease in food intake. The pharmaceutical composition according to the present invention was able to have effects of reducing the food intake, suppressing the gastric emptying, and promoting the lipolysis.

Experimental Example 3: Measurement 2 of In Vivo Activity of Example 2

This experiment was performed in the same manner as in Experimental Example 2, and then the glucose tolerance was evaluated in a mouse model using an intraperitoneal glucose tolerance test (ipGTT).

After the 2-weeks administration of the drugs was completed in the same manner as in Experimental Example 2, 2 g/kg of glucose was administered intraperitoneally to measure a change in blood glucose with the elapse of time (0, 15, 30, 60, 90, and 120 minutes). The results are listed in the following Table 6.

TABLE 6

| Time (min) | Example 2 | Positive control | Non-treated group |
|---|---|---|---|
| 0 | 40 | 109 | 118 |
| 15 | 216 | 283 | 600 |
| 30 | 172 | 202 | 522 |
| 60 | 61 | 145 | 336 |
| 90 | 48 | 124 | 236 |
| 120 | 44 | 103 | 146 |

As listed in Table 6, from the results obtained after the drugs were administered for 2 weeks, it was confirmed that a level of blood glucose sharply increased and then decreased in the non-treated group due to the administered glucose, but that an increase in blood glucose was significantly reduced in the group of mice to which the conjugate of Example 2 was administered. Therefore, it was confirmed that the glucose tolerance of the conjugate of Example 2 was increased, compare to that of the non-treated group. Also, it was revealed that an increase in blood glucose was smaller in the group of mice to which the conjugate of Example 2 was administered, compared to the positive control.

Experimental Example 4: Measurement 3 of In Vivo Activity of Example 2

To evaluate a preventing or therapeutic effect of the conjugate of Example 2 on diabetes, the conjugate of Example 2 was administered to approximately 7-week-old BKS.Cg−+Lepr$^{db}$/+Lepr$^{db}$/OlaHsd mice (db/db mice), and changes in blood glucose and body weights with time were measured.

First of all, the conjugate of Example 2 was administered to 7-week-old db/db mice by subcutaneous injection at a dose of 20 nmol/kg once every other day for 12 days. For 12 days when the drug was administered, the changes in blood glucose and body weights were measured once every other day after the drug administration. The results are listed in the following Table 7.

Next, to perform an intraperitoneal glucose tolerance test (ipGTT), 2 g/kg of glucose was administered intraperitoneally after the 12-day administration of the drug, and a change in blood glucose with the elapse of time (0, 15, 30, 60, 90, and 120 minutes) was measured. The results are listed in Table 8. To determine a degree of long-term change in average blood glucose level, a level of glycated hemoglobin (HbA1c) was also measured after the drug administration. The results are shown in FIG. 3.

TABLE 7

| | Example 2 | | Non-treated group | |
|---|---|---|---|---|
| Time (day) | Blood glucose (%) | Body weight (%) | Blood glucose (%) | Body weight (%) |
| 0 | 100 | 100 | 100 | 100 |
| 2 | 88 | 96 | 105 | 99 |
| 4 | 34 | 91 | 113 | 100 |
| 6 | 25 | 86 | 108 | 102 |
| 8 | 17 | 84 | 122 | 103 |
| 10 | 17 | 79 | 119 | 106 |
| 12 | 16 | 76 | 128 | 104 |

TABLE 8

| Time (min) | Example 2 | Non-treated group |
|---|---|---|
| 0 | 63 | 244 |
| 15 | 190 | 564 |
| 30 | 246 | 600 |
| 60 | 341 | 600 |
| 90 | 356 | 600 |
| 120 | 396 | 600 |

As listed in Table 7, it was confirmed that the body weight loss was observed in the group of mice to which the conjugate of Example 2 was administered, compared to the non-treated group. Also, it was confirmed that a high level of blood glucose was maintained for 2 weeks in the non-treated group, whereas a level of blood glucose was lowered in the group of mice to which the conjugate of Example 2 was administered.

As listed in Table 8, it was also revealed that the group of mice to which the conjugate of Example 2 was administered exhibited higher glucose tolerance than the non-treated group.

Also, as shown in FIG. 3, it was revealed that the conjugate of Example 2 was administered to significantly lower a level of glycated hemoglobin, indicating that the blood glucose was steadily maintained at a low level through the administration of the conjugate of Example 2.

Experimental Example 5: Measurement 4 of In Vivo Activity of Example 2

To check a preventing or therapeutic effect of the concentration and number of administration of the conjugate of Example 2 on obesity, the conjugate of Example 2 was administered to C57BL/6 mice, and changes in food intake and body weights with time were measured.

First, an obesity animal model was prepared by feeding a 60% high-fat diet to normal C57BL/6 mice (approximately 6 weeks old) for approximately 24 weeks, and increasing the body weights of the mice to approximately 50 g in average. Thereafter, the conjugate of Example 2 was administered to each of the groups for 2 weeks, as listed in the following Table 9. After 2 weeks, the final body weights of the mice were measured. The results are shown in FIG. 4.

TABLE 9

| Items | Method of administration |
|---|---|
| Group 1 | Example 2 is subcutaneously injected at 20 nmol/kg once every other day |
| Group 2 | Example 2 is subcutaneously injected at 40 nmol/kg once every other day |
| Group 3 | Example 2 is subcutaneously injected at 40 nmol/kg once a week |
| Non-treated group | PBS is subcutaneously injected once every other day |

As shown in FIG. 4, it was revealed that an effect of the conjugate of Example 2 on the body weight loss was more remarkable as the conjugate of Example 2 was administered at an increasing dose, and that the conjugate of Example 2 had a significant effect on the body weight loss even when administered at a low dose of 20 nmol/kg. Therefore, it was confirmed that the conjugate of Example 2 exhibited a dose-dependent response. Also, it was confirmed that, even when an interval for administration of the conjugate of Example 2 was extended once a week, the conjugate of Example 2 had the same effect on the body weight loss. Therefore, the pharmaceutical composition for preventing or treating obesity according to the present invention had a long in vivo half-life, and was able to exhibit a high level of therapeutic effect on obesity even when administered at a low dose.

Experimental Example 6: Measurement 5 of In Vivo Activities of Examples 2 and 6

To check a preventing or therapeutic effect of the conjugates of Examples 2 and 6, which had different amino acid sequences, on obesity or diabetes, an animal model of obesity was prepared by feeding a 60% high-fat diet to normal C57BL/6 mice (approximately 6 weeks old) for approximately 24 weeks, and increasing the body weights of the mice to approximately 50 g in average. Thereafter, each of the conjugates of Examples 2 or 6 was administered by subcutaneous injection at a dose of 20 nmol/kg once every other day for 2 weeks. As the control, PBS was administered instead of the conjugates of Examples. For 2 weeks when the conjugates of Examples 2 or 6 were administered, changes in blood glucose with time were measured. The results are shown in FIG. 5. Also, to perform an intraperitoneal glucose tolerance test (ipGTT), 2 g/kg of glucose was administered intraperitoneally after the 2-week administration of the drug, and changes in blood glucose with the elapse of time (0, 15, 30, 60, 90, and 120 minutes) were measured. The results are shown in FIG. 6.

As shown in FIG. 5, it was revealed that a level of blood glucose was lowered in the mice to which the conjugates of Examples 2 or 6 were administered compared to the control, but that a level of blood glucose was increased in the control to which PBS was administered.

As shown in FIG. 6, it was revealed that a level of blood glucose increased sharply and then decreased in the control due to the administered glucose, but that an increase in blood glucose was significantly reduced in the mice to which the conjugates of Examples 2 or 6 were administered for 2 weeks, compared to the control. Based on these results, it was confirmed that the glucose tolerance of the conjugates of Examples 2 and 6 was increased, compare to that of the control.

Therefore, it was confirmed that the pharmaceutical composition including the polypeptide according to the present invention had a preventing or therapeutic effect on obesity and diabetes, as shown in FIGS. 5 and 6.

Experimental Example 7: Measurement 6 of In Vivo Activity of Example 2

To check a preventing or therapeutic effect of the conjugate of Example 2 on nonalcoholic fatty liver diseases, the conjugate of Example 2 was administered to an animal model of non-alcoholic fatty liver diseases, and a level of serum cholesterol and a change in weights of the livers were checked, and a liver biopsy was conducted. The results are shown in FIGS. 7 to 9.

Specifically, first of all, a laboratory animal model of non-alcoholic fatty liver diseases was prepared by feeding a 60% high-fat diet to normal C57BL/6 mice (approximately 6 weeks old) for approximately 24 weeks, and increasing the body weights of the mice to approximately 50 g in average. Thereafter, the conjugate of Example 2 was administered by subcutaneous injection at a dose of 20 nmol/kg once every other day for 2 weeks. As the control, a GLP-1 agonist 'liraglutide' was also administered by subcutaneous injection at a dose of 100 nmol/kg daily for 2 weeks. After the 2-week administration of the drug, blood was collected from the mice to measure a serum cholesterol concentration, and the livers were extracted, weighed, embedded in paraffin, and then microtomed into thin slices. Thereafter, the liver biopsy was conducted using a hematoxylin & eosin (H&E).

Referring to FIGS. 7 and 8 in which the level of serum cholesterol and liver weights were measured, it was confirmed that the level of serum cholesterol and liver weights were significantly lowered in the mice to which the conjugate of Example 2 was administered, compared to the non-treated group to which PBS was administered, and also lowered, compared to the positive control (i.e. a liraglutide-treated group). Also, referring to the results of liver biopsy shown in FIG. 9, it can be seen that the hepatic steatosis was significantly reduced in the group of mice to which the conjugate of Example 2 was administered, compared to the non-treated group to which PBS was administered, and also reduced, compared to the positive control (i.e., a liraglutide-treated group).

As such, it was revealed that the pharmaceutical composition for preventing or treating non-alcoholic fatty liver disease according to the present invention was effective in preventing and treating non-alcoholic fatty liver disease because the pharmaceutical composition lowered the liver weight, the level of serum cholesterol, and the hepatic steatosis in the animal model of non-alcoholic fatty liver diseases.

Experimental Example 8: Measurement 7 of In Vivo Activity of Example 2

To check a preventing or therapeutic effect of the conjugate of Example 2 on nonalcoholic fatty liver diseases, the conjugate of Example 2 was administered to an animal model of non-alcoholic fatty liver diseases, and a level of serum cholesterol, the liver weights, and a change in hepatic triglycerides were measured. The results are shown in FIGS. 10 to 12.

First of all, a laboratory animal model of non-alcoholic fatty liver diseases was prepared by feeding a high-trans-fat diet, which contained 40% high fats, 20% fructose, and 2% cholesterol, to normal C57BL/6 mice (approximately 6 weeks old) for approximately 16 weeks. Thereafter, the conjugate of Example 2 was administered by subcutaneous injection at a dose of 20 nmol/kg once every three days for 4 weeks. As the positive control, a GLP-1 agonist 'liraglutide' was also administered by subcutaneous injection at a dose of 53 nmol/kg daily for 4 weeks. After the 4-week experiment was completed, a level of serum cholesterol, the liver weights, and the hepatic triglycerides (hepatic TGs) were measured.

Referring to FIGS. 10 to 12 in which the level of serum cholesterol, the liver weights, and the hepatic TGs were measured, it can be seen that the level of serum cholesterol, the liver weights, and the hepatic triglycerides were significantly lowered in the mice to which the conjugate of Example 2 was administered, compared to the non-treated group to which the saline was administered, and also lowered, compared to the positive control (i.e., a liraglutide-treated group). As such, it was revealed that the pharmaceutical composition for preventing or treating non-alcoholic fatty liver disease according to the present invention was effective in preventing and treating nonalcoholic fatty liver disease because the pharmaceutical composition lowered the liver weight, the serum cholesterol, and the hepatic triglycerides in the animal model of nonalcoholic fatty liver diseases.

Experimental Example 9: Measurement 8 of In Vivo Activity of Example 2

After the experiment was conducted in the same manner as in Experimental Example 8, a liver biopsy was conducted and an NAFLD activity score (NAS) was measured to check a preventing or therapeutic effect on non-alcoholic fatty liver diseases. An experiment was performed in the same manner as in Experimental Example 8, after the 4-week administration of the conjugate of Example 2, the mouse livers were extracted, embedded in paraffin, and then microtomed into thin slices. Thereafter, a hematoxylin & eosin (H&E) stain and an oil-red-O stain were conducted.

As a result, as shown in FIGS. 13 and 14, the liver histology and NAS results after the 4-week administration showed that the hepatic steatosis and NAS were significantly reduced in the mice to which the conjugate of Example 2 was administered, compared to the non-treated group to which the saline was administered and to the positive control (i.e., a liraglutide-treated group). As such, it was revealed that the pharmaceutical composition for preventing or treating non-alcoholic fatty liver disease according to the present invention was effective in preventing and treating nonalcoholic fatty liver disease because the pharmaceutical composition reduced the hepatic steatosis and had a lowered NAS in the animal model of non-alcoholic fatty liver diseases.

Although preferred embodiments of the present invention have been described in detail hereinabove, it should be understood that many variations and/or modifications of the basic inventive concepts herein taught which may appear to those skilled in the related art will still fall within the scope of the present invention, as defined in the appended claims.

INDUSTRIAL APPLICABILITY

The pharmaceutical composition including the polypeptide according to the present invention is useful in safely preventing or treating obesity, diabetes, or non-alcoholic fatty liver disease because the pharmaceutical composition having effects of reducing the food intake, enhancing the insulin secretion, suppressing the gastric emptying, promoting the lipolysis, and lowering a level of triglycerides without any side effects such as vomiting or nausea.

The invention claimed is:

1. A polypeptide having an amino acid sequence represented by the following General Formula 1:

[General Formula 1]
(SEQ ID NOs. 8-9)
R1-X1-QGTFTSDYSKYLD-R2-EFVQWLMNT-R3, wherein R1 is histidine, desamino-histidyl, N-dimethyl-histidyl, beta-hydroxy-imidazopropionyl, 4-imidazoacetyl, or beta-carboxy-imidazo-propionyl;

X1 is a deletion, glycine, or aminoisobutyric acid (Aib);

R2 is EQAAK (SEQ ID NO. 11), or EEAVK (SEQ ID NO. 12); and

R3 is a deletion, cysteine, lysine, or methionine.

2. The polypeptide of claim 1 in combination with a pharmaceutical excipient.

3. The polypeptide of claim 2, wherein the polypeptide is covalently bound to one or more compounds selected from the group consisting of a non-peptidic polymer, a fatty acid, cholesterol, an antibody, an antibody fragment, albumin and a fragment thereof, a nucleotide, fibronectin, transferrin, an FcRn-binding material, a saccharide, elastin, and heparin.

4. The polypeptide of claim 1, wherein R2 comprises glutamic acid (E) and lysine (K), and the glutamic acid and the lysine are taken together to form a ring via an amide bond.

5. The polypeptide of claim 3 comprising a non-peptidic polymer, wherein the non-peptidic polymer is selected from the group consisting of polyethylene glycol (PEG), polypropylene glycol, a copolymer of ethylene glycol and propylene glycol, a polyoxyethylated polyol, polyvinyl alcohol (PVA), a polysaccharide, dextran, polyvinyl ethyl ether, polylactic acid (PLA), polylactic-glycolic acid (PLGA), a lipid polymer, chitin, hyaluronic acid, and combinations thereof.

6. The polypeptide of claim 5, wherein the non-peptidic polymer is polyethylene glycol.

7. The polypeptide of claim 6, wherein the non-peptidic polymer has a molecular weight of 3,000 to 100,000 Da.

8. The polypeptide of claim 6, wherein the polyethylene glycol derivative is at least one selected from the group consisting of methoxypolyethylene glycol, methoxypolyethylene glycol N-hydroxysuccinimide, methoxypolyethylene glycol propionaldehyde, methoxypolyethylene glycol maleimide, polyethylene glycol succinimidyl propionate (PEG succinimidyl propionate), methoxy polyethylene glycol succinimidyl propionate (methoxy PEG succinimidyl propionate), acrylate polyethylene glycol succinimidyl propionate (acrylate PEG succinimidyl propionate), thiol polyethylene glycol succinimidyl propionate (thiol PEG succinimidyl propionate), hydroxy succinimidyl polyethylene glycol (hydroxy succinimidyl PEG), methoxypolyethylene glycol succinimidyl carboxymethyl ester (mPEG succinimidyl carboxymethyl ester), acrylate polyethylene glycol succinimidyl carboxymethyl ester (acrylate PEG succinimidyl carboxymethyl ester), polyethylene glycol succinimidyl carbonate (PEG succinimidyl carbonate), polyethylene glycol propionaldehyde (PEG propionaldehyde) and polyethylene glycol butyl aldehyde (PEG butyl aldehyde).

9. The polypeptide of claim 6, wherein the polyethylene glycol is linear or branched.

10. A method of preparing a pharmaceutical composition, the pharmaceutical composition comprising:
a polypeptide having an amino acid sequence represented by the following Formula 1; and
a non-peptidic polymer,
the method comprising:
mixing the non-peptidic polymer with the polypeptide to react with each other,
wherein Formula 1 is (SEQ ID NOs: 8-9)
R1-X1-QGTFTSDYSKYLD-R2-EFVQWLMNT-R3, wherein R1 is histidine, desamino-histidyl, N-dimethyl-histidyl, beta-hydroxy-imidazopropionyl, 4-imidazoacetyl, or beta-carboxy-imidazo-propionyl;

X1 is a deletion, glycine, or aminoisobutyric acid (Aib);

R2 is EQAAK (SEQ ID NO. 11), or EEAVK (SEQ ID NO. 12); and

R3 is a deletion, cysteine, lysine, or methionine.

11. The method of claim 10, wherein the R2 comprises glutamic acid (E) and lysine (K), the glutamic acid and the lysine are taken together to form a ring via an amide bond.

12. The method of claim 10, wherein the non-peptidic polymer is selected from the group consisting of polyethylene glycol (PEG), polypropylene glycol, a copolymer of ethylene glycol and propylene glycol, polyoxyethylated polyol, polyvinyl alcohol (PVA), a polysaccharide, dextran, polyvinyl ethyl ether, polylactic acid (PLA), polylactic-glycolic acid (PLGA), a lipid polymer, chitin, hyaluronic acid, and combinations thereof.

13. The method of claim 10, wherein the non-peptidic polymer is polyethylene glycol.

14. The method of claim 13, wherein the polyethylene glycol derivative is at least one selected from the group consisting of methoxypolyethylene glycol, methoxypolyethylene glycol N-hydroxysuccinimide, methoxypolyethylene glycol propionaldehyde, methoxypolyethylene glycol maleimide, polyethylene glycol succinimidyl propionate (PEG succinimidyl propionate), methoxy polyethylene glycol succinimidyl propionate (methoxy PEG succinimidyl propionate), acrylate polyethylene glycol succinimidyl propionate (acrylate PEG succinimidyl propionate), thiol polyethylene glycol succinimidyl propionate (thiol PEG succinimidyl propionate), hydroxy succinimidyl polyethylene glycol (hydroxy succinimidyl PEG), methoxypolyethylene glycol succinimidyl carboxymethyl ester (mPEG succinimidyl carboxymethyl ester), acrylate polyethylene glycol succinimidyl carboxymethyl ester (acrylate PEG succinimidyl carboxymethyl ester), polyethylene glycol succinimidyl carbonate (PEG succinimidyl carbonate), polyethylene glycol propionaldehyde (PEG propionaldehyde) and polyethylene glycol butyl aldehyde (PEG butyl aldehyde).

15. The method of claim 10, wherein the mixing of the non-peptidic polymer with the polypeptide to react with each other comprises allowing the polypeptide and the non-peptidic polymer to react at a molar ratio of 1:1 to 1:5.

16. The method of claim 10, wherein the mixing of the non-peptidic polymer with the polypeptide to react with each other is performed at pH 4.0 to 9.0.

17. The method of claim 10, wherein, in the mixing of the non-peptidic polymer with the polypeptide to react with each other, the reaction time is in a range of 0.5 to 24 hours.

* * * * *